United States Patent [19]

Hildenbrand et al.

[11] Patent Number: 4,824,639

[45] Date of Patent: Apr. 25, 1989

[54] TEST DEVICE AND A METHOD FOR THE DETECTION OF A COMPONENT OF A LIQUID SAMPLE

[75] Inventors: Karlheinz Hildenbrand, Krefeld; Hans-Hagen von Döhren, Bochum-Langendreer; Hermann Perrey, Krefeld, all of Fed. Rep. of Germany; Georg Frank, Elkhart, Ind.; Rolf Dhein, Krefeld, Fed. Rep. of Germany

[73] Assignee: Bayer Aktiengesellschaft, Leverkusen, Fed. Rep. of Germany

[21] Appl. No.: 151,779

[22] Filed: Feb. 3, 1988

Related U.S. Application Data

[63] Continuation of Ser. No. 35,821, Apr. 8, 1987, abandoned, which is a continuation of Ser. No. 704,825, Feb. 25, 1985, abandoned.

[30] Foreign Application Priority Data

Feb. 29, 1984 [DE] Fed. Rep. of Germany ....... 3407359

[51] Int. Cl.$^4$ .................... G01N 31/22; G01N 33/483
[52] U.S. Cl. ........................ 422/56; 422/57; 422/58; 436/169; 435/805
[58] Field of Search ............................ 422/56, 57, 58; 436/169, 170, 177; 435/805; 210/506, 927

[56] References Cited

U.S. PATENT DOCUMENTS

| | | | |
|---|---|---|---|
| 3,607,093 | 9/1971 | Stone . | |
| 3,847,822 | 11/1974 | Shuey | 210/500.28 |
| 3,852,388 | 12/1974 | Kimura | 210/500.33 X |
| 3,992,158 | 11/1976 | Przybylowicz | 422/57 |

FOREIGN PATENT DOCUMENTS

| | | |
|---|---|---|
| 0064710 | 11/1982 | European Pat. Off. . |
| 0071169 | 2/1983 | European Pat. Off. . |
| 2332760 | 1/1974 | Fed. Rep. of Germany . |
| 2602975 | 8/1976 | Fed. Rep. of Germany . |

OTHER PUBLICATIONS

FDA Medical Device Standards Publication Technical Report "Proposed Performance Standard for in vitro Diagnostic Devices Used in Quantitative Measurement of Glucose in Serum or Plasma".

Amicon Ultrafiltration Membranes Brochure, Aug. 1980.

Ullmanns Encyklopädie der Technischen Chemie, p. 518.

*Primary Examiner*—Barry S. Richman
*Assistant Examiner*—Jill Johnston
*Attorney, Agent, or Firm*—Sprung Horn Kramer & Woods

[57] ABSTRACT

In a test strip for the detection of a component in a liquid sample, the strip comprising a support layer, a microporous polymer layer and a reagent for the detection of the component to be determined, the improvement wherein the microporous polymer layer is a membrane which has an asymmetric pore structure with the narrower pores being on the side to which the sample is applied, and the support layer is macroscopically smooth. The porous membrane is produced by coagulation from solution.

17 Claims, No Drawings

TEST DEVICE AND A METHOD FOR THE DETECTION OF A COMPONENT OF A LIQUID SAMPLE

This is a continuation of application Ser. No. 035,821 filed Apr. 8, 1987 now abandoned which in turn is a continuation of application Ser. No. 704,825 filed Feb. 25, 1985, now abandoned.

The present invention relates to an improved analytical element for the spectrophotometric analysis of a component of a fluid, in particular a body fluid. The analytical element according to the invention is characterized by having at least one asymmetric membrane produced by the coagulation process.

The determination of a component of a fluid using "dry" reagents (for example test strips) is becoming of increasing importance, in particular in clinical diagnosis. Thus, the detection of certain components of urine, serum or blood, such as glucose, bilirubin, urea or proteins, is increasingly carried out using test strips. Compared with conventional wet chemical methods, analyses of this type are more rapid, more straightforward and more reasonably priced.

In the test strips customarily used for liquid samples, the reagents necessary for the determination of the analyte sought are contained in a suitable fluid-absorbing support material. When the liquid sample is applied to this support, diffusion of the fluid into the support (reaction space) takes place, whereupon the detection reagents produce, with the sample component to be analyzed, for example a specific, concentration-dependent coloration.

The fluid-absorbing support materials initially used were simple papers, and those used subsequently were chemically modified papers which were impregnated with the detection reagents. However, because of their lack of homogeneity in respect of layer thickness and composition, papers are poorly suited for quantitative determinations.

The use of polymeric support materials by means of suitable coating techniques represented an important advance in diagnosis using quantitative test strips.

Thus, a multi-layer test device comprising a transparent support, a gelatin layer and a microporous cellulose acetate layer containing filler is described in DE-AS (German Published Specification) No. 2,332,760. The gelatin layer contains the reagents and thus acts as the reaction and detectin zone. The function of the microporous cellulose acetate layer is the homogeneous distribution of the sample, the removal of the erythrocytes, and the reflection of the measurement radiation incident from the side of the support.

One advantage of test devices containing gelatin layers is that the coating techniques used for their production are known from photography and are industrially well developed. A disadvantage of such systems, as it is for other test devices which contain polymers which swell in water (for example agarose), is that swelling processes take place in addition to the detection reaction so that the reaction does not come to a standstill until after a lengthy period. Thus, for rapid analysis it is possible to use only the kinetics of the reaction, not end-point determination. In order to make quantitative analyses possible, the sample must be metered in. Moreover, gelatin is not ideal because of the limited stability of the biochemical detection reagents in gelatin, and because of the limited stability of the coloration formed in the detection reaction (thus, delaying evaluation of the analysis for several days is not possible). In addition, gelatin is sensitive to proteases which customarily occur as an impurity in the enzymes necessary for the detection reaction.

Another test strip system based on polymers for the determination of constituents in body fluids is described in European patent application Ser. No. 0,064,710. In this instance, the matrix used for the reagents is a porous polymer film produced by drying a latex (for example an aqueous dispersion of polyvinyl propionate) in the presence of an expanding agent (for example silica gel). The liquid sample to be analyzed is applied directly to the reagent layer which is located on a PVC film. After a certain time, the excess sample and erythrocytes are wiped off, and the color reaction is observed or determined by reflectometry from the side facing away from the support.

An unsatisfactory feature of this system (and quite generally for systems in which the sample is directly applied to the reagent layer) is so-called bleeding. This means that detection reagents from the reagent layer, in particular water-soluble ones (for example enzymes), can dissolved in the excess sample, and these are then removed from the system on wiping, and this leads to falsification of the results. For this reason, it is also of interest to develop test strips in which evaluation via a transparent support is possible, so that it is possible to dispense with wiping off the sample.

Other disadvantages of the sytem of European Patent A No. 64,710 are that the sample must be allowed to act for a relatively long time (for example 2 min.), and that it is difficult to produce specific, in particular relatively large, pores (in the $\mu$m range). Large-pored systems of this type would be of particular interest for the detection of high molecular weight analytes.

The aim of the present invention is to develop a new test agent, in particular for components in whole blood, which is straightforward to manipulate and provides results which are as quantitative as possible. Straightforward manipulation is important to the extent that diagnosis using test strips is being increasingly employed by non-specialists for whom there are difficulties with, in particular, exact metering of the amount of sample or wiping off the excess sample after defined times.

It should be possible straightforwardly to produce the test agents of constant quality, and it should have the following properties, in particular:
  reproducible dependence of the color reaction on the analyte concentration;
  intensive coloration;
  rapid reaction (end-point determination);
  evaluation from the support side and (after wiping) from the application side;
  measurement of whole blood possible;
  good stability of the colors and the entire system;
  straightforward production of specific pore sizes;
  analytical values independent of the sample volume applied;
  non-swelling polymer matrix;
  no bleeding.

It has now been found, suprisingly, that test devices having polymer layers for sample application can be produced by the method of membrane production by coagulation of polymer solutions, and these, alone or combined with other elements, meet all the requirements of clinical diagnosis without exhibiting the abovementioned deficiencies. Thus, a large number of polymer systems of a wide variety of chemical constitutions (for example hydrophilic; hydrophobic; acid or basic ion exchanger groups), which permit specific separations and are not biologically degradable, are suitable for the production of membranes by the coagulation method. In addition, it is possible, using the production process, to produce membranes having a variety of defined pore sizes and pore volumes, and thus the specific separation of interfering constituents is made possible, and the system acts in a self-metering fashion.

The present invention relates to a test device for the detection of a component in a liquid sample, in particular in a body fluid such as blood or urine, the device comprising a support layer, a microporous polymer layer, where appropriate other layers, and reagents, incorporated in one or more of the layers, for the detection of the components to be determined. The invention is characterized by, on the one hand, the use of a microporous polymer layer which is a membrane produced by the coagulation method and has an asymmetric pore structure, the pores narrowing toward the side of the test device which is intended for application of the sample, and by, on the other hand, the use of a macroscopically smooth support layer which is preferably impermeable to the sample under the test conditions.

Microporous films composed of completely synthetic polymers which can be produced with defined pore volumes and variable pore sizes are suitable and preferred according to the invention. The completely synthetic nature of the polymers is important for the reason that, in contrast to natural or semi-synthetic polymers, they can be produced with high reproducibility and they permit straightforward quality control.

Microporous polymer films (membranes) which are employed for the large-scale industrial separation of molecular mixtures by using an external pressure have been known for some time and are commercially available. There are several processes for the production of membranes of this type, the so-called "phase-inversion method" having achieved the greatest importance. Information on the fundamentals of these techniques is to be found in, for example, H. Strathmann, "Trennungen von molekularen Mischungen mit Hilfe synthetischer Membranen" (separation of molecular mixtures using synthetic membranes), Steinkopfverlag Darmstadt (1979).

There is a variety of variants within the phase-inversion process. In the coagulation process, the procedure in principle is such that a solid support is coated with a polymer solution (casting solution) of uniform thickness (for example 100 $\mu$m), where appropriate exposed to an atmosphere which contains a non-solvent (preferably water) for the polymer in the form of vapor, until the solution has partially or completely gelled, and then immersed in a coagulation bath, whereupon a solid, mircoporous film with an asymmetrical structure is produced. If the membrane film remains adherent to the solid support during the coagulation (when specially porous polymer bonded webs or polymer films are used), then supported membranes are obtained. If the membrane film becomes detached from the solid support during the coagulation (for example when glass is used), the unsupported membranes are produced. The nature of the coagulation fluid is such that it is miscible with the solvent in the casting solution, but is a precipitant for the polymer. A typical feature of this variant is that the coagulation (pore-formation) essentially only takes place on immersion in the coagulation fluid, and that asymmetrical membrane structures are produced. In this context, asymmetrical denotes that the pores—regarded from the underside of the membrane (support side)—narrow toward the surface of the membrane.

As a rule, the ratio of the mean pore diameter on the underside of the membrane to that on the surface of the membrane in these cases (which can be determined by, for example, electron microscopic films) is greater than 5:1, preferably greater than 10:1, greatly preferably greater than 30:1. As has emerged, the use according to the invention of membranes of this type has the advantage that blockage of the pores is prevented when the product is applied to the surface of the membrane.

The majority of commercially available membranes are produced by this process. It has already been proposed that membranes of this type be used directly as a support matrix for detection systems (U.S. Pat. No. 3,607,093) by subsequently impregnating the finished membranes with the test reagents. However, the commercially available supported membranes do not meet the requirements of reproducibility which are set in practice.

This is because the membranes are located on porous bonded web supports, composed of, for example, polyethylene, polypropylene or polyester, which are not macroscopically smooth. Hence the membrane layer thickness, and thus the pore volume, is subject to relatively large fluctuations which lead to variations in the detection reaction. In addition, the consequence of the porous, fluid-absorbing nature of the bonded web support is that not just the pore volume of the membrane is responsible for the amount of fluid absorbed but also the porous supports which absorbs fluid because of capillary forces.

Unsupported asymmetrical membranes have not hitherto been used or proposed for the production of test devices. However, they are less preferred according to the invention since they are difficult to manipulate and can, as a rule, only be dried when they are impregnated with preservatives. Thus, in the production of a test agent, they require another operation step, namely attachment to a support. It is possible to use adhesives for this purpose, but these may lead to further complications (for example partial dissolution of the membrane; absorption of fluid).

The incorporation of the detection reagents into the finished membranes is carried out by impregnation using the system described in U.S. Pat. No. 3,607,093. Since, as a rule, both organic and water-soluble reagents have to be incorporated, both impregnation in organic solution and impregnation in aqueous solution are necessary.

Thus, there is a restriction to membranes which are resistant to the appropriate organic solvent. In addition, systems of the type which are merely impregnated with the detection reagents tend to bleed.

Another variant of membrane production by the phase-inversion method is based on dissolving a polymer in a mixture of a good, readily vaporized solvent and a poor, higher boiling solvent. If a solution of this type is spread out to form a film, and heat is applied, then the good, low boiling solvent evaporates first, while the poor solvent for the polymer accumulates and induces the system to coagulate. Then, if required to wash out the remainder of the high boiling solvent, the membrane can also be immersed in a liquid bath which, however, in contrast to the coagulation in a precipitation bath described above, does not essentially contribute to the formation of the membrane.

Asymmetrical structures are not obtained by this method. In addition, in practice it is possible to use only those polymers for which there exists a good, low boiling solvent, and this greatly limits the selection of polymers. Thus, in practice to date, only the semi-synthetic cellulose derivatives (for example cellulose acetate, cellulose nitrate), for which acetone is a very good solvent, have been processed into membranes using this method. For example, the filter layers of cellulose acetate ("blush polymer layers") located on gelatin layers, which were used in accordance with DE-AS (German Published Specification) No. 2,332,760, were produced in the solvent system acetone/toluene.

As described in DOS (German Published Specification) No. 2,602,975, this method has also already been used for the production of single-layer detection systems, the reagents being incorporated in the polymer solution. Thus, using this process, porous membranes containing the detection reagents have been obtained directly. The test elements are produced in accordance with DOS (German Published Specification) No. 2,602,975 on a glass plate, from which, after drying, the membranes are detached and are glued to a plastic film. This results in the difficulties of unsupported membranes described above. It is also described in DOS (German Published Specification) No. 2,602,975 that it is possible to produce the detection systems directly on an integral substrate by replacing the glass plate by a polymer film, which needs to be of such a nature that it reacts chemically or physically with the solvent system used, fusion of the membrane with the support film occurring. However, very few variations of this process are possible, since the composition of the solvent and the evaporation time have to be selected to accord with the desired porosity of the membranes to be produced. Accordingly, the effect on the support will differ in its extent depending on whether it is desired to produce membranes with fine pores or with coarse pores. As a rule, in the case of transparent supports, the permeability to light is also impaired due to the partial dissolution, and thus evaluation from the support side is difficult.

In addition, as a rule polymer films which are attacked by solvents undergo irreversible changes, such as swelling, shrinkage or irregularities, especially when the contact between the solvent and the polymeric support lasts a relatively long time, which is the case in the type of membrane production described there. Accordingly, this method is not suitable for the production of supported microporous polymer films which are intended to meet the requirements for reagent supports.

Details of the production of microporous sheet-like structures by the coagulation process to be used according to the invention are given in a large number of publications. Thus, in German Patent Specification No. 1,110,607, it is proposed for the coagulation of polyurethanes based on polyethers that hygroscopic polyurethane solutions (an example of a solvent used for this is dimethylformamide) be exposed to the action of an atmosphere containing water vapor, which is, where appropriate, made to circulate and which has a relative humidity of 15 to 100% at a temperature of the dry thermometer of 10° to 38° C. Because of the absorption of water as a result of the hygroscopicity of the solvent, the polyurethane starts to precipitate out of the solution from the direction of the surface, probably with preformation of the microporous structure. When films or coatings pregelled in this manner are placed in water, the hygroscopic solvent is completely removed from the film, with coagulation of the solution.

DE-OS (German Published Specification) No. 1,444,163 indicates a somewhat modified process: the polyurethane solution is first, by addition of minor amounts of nonsolvents (for example water), converted into a state of incipient phase separation, that is to say in a slightly cloudy form resembling a dispersion, before it is coagulated (after spreading out in the form of a sheet) directly, that is to say without pregelling in a moist atmosphere, by immersion in the non-solvent.

Another process is indicated in DE-OS (German Published Specification) No. 1,444,165, according to which the polymer solution can be converted into microporous films, without pregelling, by indirect coagulation in a mixture of non-solvent and solvent (for example dimethylformamide/H$_2$O in a mixing ratio between 10:90 and 95:5).

According to another variant, which is described in Belgian Patent Specification No. 624,250, sufficient nonsolvent is added to the polymer solution for the polymer to separate out as a gel. It is only this gel which is then spread onto a substrate and coagulated with non-solvent (water) to give a microporous structure.

It is indicated, in DE-AS (German Published Specification) No. 1,238,206, that direct coagulation of elastomer solutions leads to microporous structures when the coated substrates are coagulated in baths which are heated to the neighborhood of the boiling point of the fluid in the bath, for example in hot water at 95° C.

Improved results are obtained when the pregelling is also carried out at elevated temperature. Thus, DE-OS (German Published Specification) No. 2,025,616 describes a process for the production of microporous sheet-like structures in which a thin layer of a polyurethane solution is exposed to an atmosphere of water vapor with a relative humidity of at least 50%, at temperatures above 65° C., and then the major amount of the solvent is removed in aqueous coagulation baths, and the product is then dried.

According to DE-OS (German Published Specification) No. 2,125,908, water vapor at a temperature between 101° C. and 190° C. is passed over a layer of a polyurethane solution until the content of organic solvent in the layer has decreased to less than 50% by weight, and the layer has been converted into a solid, mechanically stable microporous sheet-like structure. This process has the particular advantage that a microporous final product results from a polyurethane solution in a short time and in a single process step.

It is possible in the processes mentioned to add certain coagulation aids to the polymer solutions with the object of improving the coagulability. Thus, DE-AS (German Published Specification) No. 1,270,276, DE-OS (German Published Specification) No. 1,694,171 and DE-O (German Published Specification) No. 1,769,277 describe processes for the production of sheet-like structures which are permeable to water vapor in which solutions of 90 to 70 parts by weight of polyurethanes or polyureas and 10 to 30 parts by weight of high molecular weight, essentially linear, cationic polyurethanes, which contain 0.5 to 2.0% by weight of quaternary ammonium nitrogen atoms, are, where appropriate after gelling in moist air, coagulated with water or a mixture of water and solvent. In addition to the cationic polyurethanes, these solutions can also contain anionic tanning agents as additional coagulation regulators.

According to DE-OS (German Published Specification) No. 2,427,274, in many cases it is possible to achieve a further improvement by the polyurethane solutions to be coagulated containing certain cationic or anionic polyurethane/urea suspensions alone or, preferably, simultaneously cationic and anionic polyurethane (urea)s in salt form. It is possible in this manner to control, in such a manner that sheet-like structures of satisfactory microporosity are produced, the coagulation even of polyurethane solutions which are difficult to process.

Using the processes described in the references mentioned, it is possible to produce microporous membranes from virtually every soluble polymer, it being possible to achieve specific pore sizes by means of various parameters (for example in the concentration of the casting solution, the temperature, additives, the nature of the coagulation fluid)—where appropriate after a few preliminary tests.

Moreover, the advantages of the present invention result from these possibilities. Thus, it is possible in a straightforward manner to adjust the composition and porosity of the polymeric membrane to suit the intended detection system.

In most cases, it is preferred according to the invention that the coagulation is carried out directly in an aqueous coagulation bath, that is to say without special pretreatment.

The properties of the detection elements according to the invention (homogeneity and intensity of the color reaction, bleeding, stability of the detection system, possibility of wiping off erythrocytes, and rate of the detection reaction) are very dependent on the type of polymer system used.

In order to meet the requirements of straightforward production by machines, defined pore volume and evaluation from the rear side of the support, the polymer casting solutions which are preferably used according to the invention are such that the membranes can be produced directly on a macroscopically smooth, impermeable support. If the casting solutions of conventional membranes (for example cellulose acetate or polysulphone are applied to smooth, impermeable films, then the solid film which is produced during the coagulation detaches from the support if the support is not attacked to a sufficient extent by the solvent that it fuses with the membrane). However, this leads to variation in the results of measurement. In order to avoid this problem, it is necessary in the direct production of supported membranes to suit the system of casting solution and support to one another in such a manner that the casting solution has a high affinity for the support but does not attack it, that is to say dissolve it.

The polymer systems which have proved to be favorable are those which can be modified in respect of their hydrophilicity/hydrophobicity balance in a manner known per se. In this connection, polymers having ionic groups are particularly advantageous, and these can, where appropriate, also be used as a component in a polymer mixture. The hydrophilic (or hydrophobic) properties of the polymer membranes can be of importance for, example, the optimization of the color reaction (the color is frequently more intense when the polymer contains ionic groups).

Examples of polymers from which it is possible to prepare suitable casting solutions for the detection elements claimed according to the invention are:
polyamides, polyamides having disulphimide groups

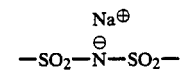

(see, for example, U.S. Pat. No. 4,269,967), polyether carbonates (see, for example, DE-OS (German Published Specification) No. 2,251,066), polyacrylonitrile and polyurethanes, as are described in, for example, DE-OS (German Published Specification) No. 2,427,274 and the printed material cited there.

Preferred casting solutions are obtained when the solutions of the polymers mentioned are mixed with aqueous polymer dispersions known per se, which preferably have ionic groups, for example composed of polyvinyl compounds, vinyl copolymers, polystyrenesulphonic acids, polyamides or polyurethanes. Casting solutions which consist of mixtures of polyurethane solutions with aqueous polyurethane dispersions (see, for example, Angew. Makromol. Chem. 98 (1981) 133 and DE-OS (German Published Specification) No. 2,427,274, which has already been mentioned, and the references cited there) are very particularly suitable. The polyurethane dispersions can be non-ionic or, preferably, ionic, it being possible for the ionic radicals to be, for example, $-SO_3^-$, $-COO^-$ or $-N^+R_3$ groups.

Ionic polymer systems are particularly preferred since they show good adhesion to the support film and immobilization of the enzymes necessary for the detection reaction. The detection systems according to the invention which are based on ionic polymers can be rinsed with water for several hours without the occurrence of any bleeding worth mentioning.

The solvents used for the preparation of the casting solution are those customary for the particular polymers, such as, for example, dimethylformamide, N-methylpyrrolidone or dioxolane, it being possible, where appropriate, for inorganic salts which are soluble in the casting solution, such as LiCl, $CaCl_2$ or $Mg(ClO_4)_2$, to be added as expanding agents. It is also possible to add, as further additives, substances which are insoluble in the casting solution and which serve as fillers, such as $SiO_2$, $TiO_2$ (see European patent application No. 0,077,509), $BaSO_4$, ZnO or cellulose or agarose powder, on which, where appropriate, biologically active material is immobilized.

Supported microporous detection elements according to the invention are produced by uniformly coating a suitable support with a casting solution of this type (layer thickness about 50–100 μm) and then, preferably immediately, immersing it in a coagulation bath, whereupon the microporous supported polymer films are produced. The time between the coating of the support and the coagulation is kept as short as possible (about a few seconds) so that the support is not attacked by the solvent in the casting solution. Examples of suitable coagulation fluids are water or aqueous buffer solutions which can, where appropriate, also contain plasticizers, for example glycerol.

The pore structure can be modified in a straightforward manner by the nature of the coagulation bath. Thus, from just one casting solution, increasing pore sizes on the membrane surface can be achieved by precipitation in water at increasing temperatures, as can be shown by SEM photographs of microporous polymer films which were coagulated at room temperature, 45° C. and 60° C. Similar effects can also be achieved by using mixtures of water with organic solvents, for example water/dimethylformamide.

Supports which are suitable for the detection elements according to the invention are, in principle, macroscopically smooth polymer films on which the polymer system used shows good adhesion during coagulation as well as after drying, and which undergo no change by the polymer casting solution. Transparent polymer films which also permit evaluation of the color reaction through the side of the support are particularly preferred. Transparent polyethylene terephthlate films are very particularly preferred.

The reagents necessary for the detection reaction can be introduced into the microporous polymer films in a variety of ways, for example by stirring them into the casting solution, by subsequent impregnation of the porous films, or by a combination of these two processes.

According to a preferred variant, enzyme-containing reagent systems for the detection of an analyte, which are known per se, are introduced into the test devices according to the invention.

A straightforward method for the production of microporous polymer films loaded with detection reagents comprises, for example, dissolving the chromogen used (for example 3,3',5,5'-tetramethylbenzidine) in the casting solution, and processing the latter by the coagulation process to give a chromogen-loaded microporous film which is then impregnated with the enzyme system (buffered where appropriate).

The test agents according to the invention can also be designed as a multi-layer system. This is an advantage when the detection reagents have to be separated. For example, a support film can be provided with a polymer layer onto which is then applied the asymmetric membrane using the coagulation method described, or a separately produced, unsupported, finished membrane is laminated on.

Where appropriate, all or part of the detection reagents can be incorporated in the polymer layer located between the support and the membrane, the other part of the detection reagents being located in the membrane located above.

Examples of suitable polymeric intermediate layers into which the detection reagents can, where appropriate, be incorporated (reagent layer), are films known per se and derived from aqueous dispersions belonging to the class of polyvinyl compounds, of vinyl copolymers, of polystyrenesulphonic acids, of polyamides or of polyurethanes. Since the reagent-containing layer should preferably be soluble, or at least swellable, in water, polyurethane dispersions which are, where appropriate, mixed with polymers which are soluble in water or swellable with water, such as polyvinyl alcohol, polyethylene glycol, cellulose ethers, polyacrylamide, polyacrylic acid or polyvinylpyrrolidone, are particularly suitable. Very particularly preferred reagent layers are obtained from mixtures of ionic polyurethanes dispersions with polyvinylpyrrolidone.

After wiping off the excess sample, the color reaction can be observed from the application side (membrane surface) or, when transparent supports are used, from the support side, in which case the excess sample need not be wiped off. In the latter case, it is preferable for the chromogen to be located in a reagent layer between the membrane and the transparent support.

The detection elements according to the invention are suitable for the quantitative determination of low and high molecular weight components in liquid samples, in particular for the quantitative spectrophotometric detection of constituents of body fluids, such as, for example, bilirubin, ketones, triglycerides, urea or haemoglobin. As the examples which follow show, the detection systems according to the invention are very particularly suited for the quantitative detection of glucose in whole blood, and for the detection of enzymes, such as glucose oxidase or cholinesterase, and the detection of bilirubin or ketone bodies.

In the examples, unless otherwise noted amounts indicated are to be understood to be parts by weight or percentages by weight.

EXAMPLE 1

Detection of Glucose

Using a high speed stirrer (dissolver), a casting solution of the following composition was prepared:
8.02 g of disulphimide-polyamide
2.40 g of CaCl$_2$
43.02 g of dimethylformamide (DMF)
0.01 g of ascorbic acid
0.01 g of sodium citrate
0.40 g of citric acid
0.48 g of 3,3',5,5'-tetramethylbenzidine
45.40 g of titanium dioxide
0.13 g of peroxidase (POD, 277 U/mg)
0.13 g of glucose oxidase (GOD, 116 U/mg).

Using this casting solution, a polyethylene terephthalate film was uniformly coated in a spreading thickness of 100 μm using a doctor knife. This supported film was coagulated in a 30% strength aqueous glycerol bath for 10 min. The solid supported membrane thus produced was dried with warm air (35° C.) and tested for its functioning with whole blood. The blood was applied to the membrane surface, and wiped off after 1 minute. A homogeneous green coloration had developed on the membrane surface about 30 sec. after wiping off.

The disulphimide-polyamide is a polycondensate, produced in a one-pot reaction in accordance with U.S. Pat. No. 4,269,967, of the following:

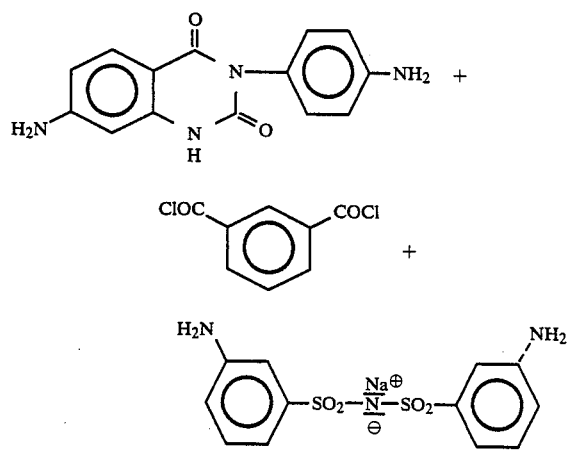

EXAMPLE 2

Detection of Glucose

Casting solution:
13.73 g of polyurethane
66.37 g of dimethylformamide
7.24 g of polyurethane dispersion in water/DMF
0.07 g of sodium dioctyl sulphosuccinate
11.01 g of titanium dioxide
0.79 g of 3,3′,5,5′-tetramethylbenzidine
0.79 g of ascorbic acid.

The polyurethane used is a thermoplastic material which was obtained by reaction of 75 parts of a polyester of adipic acid, 70 mol % of ethylene glycol and 3 mol-% of 1,4-butanediol (MW=2,000), 25 parts of a polyester of adipic acid and 1,4-butanediol (MW=2,250), 25 parts of 1,4-butanediol and 85 parts of dimethylmethane diisocyanate.

The polyurethane dispersion serves as a coagulation aid and is a cationic dispersion, containing no emulsifier, of a reaction product of
  200 parts of a polyester of adipic acid, phthalic acid and ethylene glycol (MW=1,700),
  50 parts of toluylene diisocyanate,
  20 parts of N-methyldiethanolamine and
  6 parts of p-xylylene dichloride.

The supported, microporous polymer membrane was produced as in Example 1 with the following modifications: Support: polyethylene terephthalate film Coagulation bath: 1% strength solution of Na lauryl sulphate.

After drying, the film was impregnated for 1 minute with a 1% strength solution of POD (277 U/mg)/GOD (116 U/mg) in citrate buffer (pH 5.5) and was dried.

Test with whole blood: 10 sec. after application of the sample, a homogeneous blue coloration was observable through the transparent support, likewise after wiping off the excess sample on the membrane surface.

With 0.05, 0.1 and 0.5% strength glucose solutions, homogeneous blue colorations were produced immediately, and these showed increasing intensities of color (color gradations) appropriate for the increasing glucose concentration.

Accordingly, graded reflection values were measured on evaluation by reflectometry of various glucose concentrations. In addition, the measurements showed that the coloration is linearly dependent on the glucose concentration in the range from 20 to 800 mg glucose/dl water, and that the end point of the detection reaction is reached after 40 seconds at the most. Compared with known test devices, this has to be regarded as being extremely rapid.

Examinations by electron microscopy (SEM) of the test strip system described in Example 2 showed that the membrane was highly porous, the mean pore size being 0.5μ.

EXAMPLE 2a

Test Strips for Bilirubin

Casting solution and production of the membrane as in Example 2, but without TMB and ascorbic acid.
The polymer membrane was impregnated with
1.68 g p-toluenesulphonic acid,
0.18 g of disodium salt of naphthalene-1,5-disulphonic acid,
2.00 g of 7-(2,3-dihydroxypropyl)theophylline,
0.06 g of sodium nitrite and
0.10 g of saponine
in 9 ml of distilled water
and dried.

The test strips produced from the impregnated membrane develop brown colors of varying intensity after application of various concentrations of a bilirubin control serum.

EXAMPLE 2b test Strips for Ketone Bodies

Casting solution and production of the membrane as in Example 2, but without TMB and ascorbic acid.
The polymer membrane was, after a pH of 9.4 had been set up, impregnated with
2 g of sodium nitroprusside and
8.2 g of magnesium sulphate
in 11 ml of distilled water
and dried.

After immersion of the cut test strips in acetoacetic acid solutions or urine, the test strips developed violet colors of varying intensities depending on the concentration of ketone bodies.

EXAMPLE 3

Detection of Glucose

Two-layer system
(A) Production of a supported reagent layer
8.40 g of aqueous polyurethane dispersion
3.00 g of polyvinylpyrrolidone (MW 350,000)
0.50 g of tetramethylbenzidine (dissolved in 1 g of ethyl acetate)
0.12 g each of glucose oxidase (116 U/mg) and peroxidase (277 U/mg) and
0.025 g of ascorbic acid
are stirred together, and coated onto a polyester film and dried with warm air, a supported reagent layer being obtained.

The polyurethane dispersion is a 40% strength aqueous dispersion of a reaction product of
  82 parts of a polyester of adipic acid, hexanediol and neopentyl glycol (MW=1,700),
  15 parts of hexamethylene diisocyanate,
  2 parts of Na ethylenediamine ethanolsulphonate and
  1 part of ethylenediamine.

With aqueous glucose solutions, these supported reagent layers developed, about 20 sec. after application of the sample, homogeneous colorations which were graded with different glucose concentrations (see Example 2).

(B) Application of an asymmetric phase-inversion membrane
  (a) all detection reagents in the reagent layer
The casting solution described in Example 2, but which did not contain the tetramethylbenzidine and ascorbic acid described there, was coated onto the supported reagent layer described in Example 3A), and was coagulated in 1% strength aqueous Na lauryl sulphate solution.

After drying with warm air, it was tested with aqueous glucose solutions and with whole blood. Homogeneous, concentration-dependent blue colorations were observed from the support side about 30 seconds after application of the sample.

(b) Reagents in various layers
A supported, enzyme-containing layer was produced in analogy to Example 3A) from
  8.40 g of aqueous polyurethane dispersion (see Example 3)

3.00 g of polyvinylpyrrolidone (MW 350,000) and
0.12 g each of glucose oxidase (116 U/mg) and peroxidase (227 U/mg).

The casting solution described in Example 2 was coated onto this, and coagulated in 1% strength Na lauryl sulphate solution and dried. On testing with whole blood, a homogeneous blue coloration was observed from the application side about 40 sec. after application of the sample and wiping off the erythrocytes. Graded blue colorations were developed with glucose solutions of different concentrations.

EXAMPLE 4

Detection of Glucose

Two-layer system with reagent layer.
Casting solution for the reagent layer:
8.00 g of the polyurethane dispersion from Example 3
1.00 g of polyvinylpyrrolidone (MW 10,000)
0.05 g of tetramethylbenzidine dissolved in 10 g of ethyl acetate
0.10 g of glucose oxidase (116 U/mg) dissolved in 2 ml of water
0.10 g of peroxidase (227 U/mg)
0.01 ml of a 5% strength aqueous solution of ascorbic acid were stirred together, coated onto a polyethylene terephthalate film and dried with warm air (=supported reagent layer).

A polyamide membrane produced by the phase-inversion process from the following casting solution was applied to this supported reagent layer:
8.10 g of polyamide (polycondensation product of hexamethylenediamine and isophthalic acid according to DE-OS (German Published Specification) No. 2,743,515)
2.40 g of $CaCl_2$
43.00 g of dimethylformamide and
46.00 g of $TiO_2$
Coating thickness: 100 μm
Coagulation bath: 30% strength aqueous glycerol solution Test with whole blood: one drop of blood was applied to the membrane surface. About 10 sec. after application of the sample, a homogeneous blue coloration was observed through the transparent support. Graded blue colorations were developed with glucose solutions of various concentrations (see Example 2).

EXAMPLE 5

Detection of Glucose

Membrane with reagent layer
Casting solution for the membrane:
20.00 g of polysulphone (condensation product of bisphenol A and bis(chlorophenylsulphone); Udel P 1700; commercial product of Union Carbide) was dissolved in
80.00 g of N-methylpyrrolidone.

The casting solution was applied with a doctor to a glass plate (100 μm) and immersed for coagulation in an aqueous 10% strength glycerol bath. During this, the film detached from the glass support, and an unsupported, asymmetrical membrane was obtained.

After drying, the rear side (side of the film which had been located on the support) of the polysulphone membrane was coated with the reagent layer described in Example 4.

Test with whole blood: one drop of blood was applied to the membrane surface. About 30 sec. after application of the sample, a homogeneous blue coloration was observed in the reagent layer. Graded blue colorations were developed with glucose solutions of various concentrations.

EXAMPLE 6

Enzyme Detection

The membrane described in Example 2 was, after being dried, impregnated with a 1% strength aqueous glucose/POD (277 U/mg) solution and dried.

In tests with dilute GOD solutions (20 U/ml; 40 U/ml; 80 U/ml; 120 U/ml; 160 U/ml), immediately after application of the sample a homogeneous blue coloration, which was graded in accordance with the GOD concentration, was observed on the membrane surface as well as through the transparent support.

EXAMPLE 6a

Test Strips for Cholinesterase

Casting solution and production of the membrane as in Example 2, but without the TMB and ascorbic acid.

The membrane was impregnated with a solution of 40 mg of indoxyl acetate in 5 ml of ethyl acetate and 120 mg of 2-methoxy-4-morpholinobenzenediazonium chloride.$ZnCl_2$ in 5 ml of methanol, and then again with tris HCl buffer (0.4M; pH 7.5), and was dried and then processed to form test strips.

After application of chlolinesterase solutions and serum, the test strips developed blue colorations at different rates depending on the enzyme activity. The coloration can be quantitatively evaluated using a reflection measuring apparatus.

It will be understood that the specification and examples are illustrative but not limitative of the present invention and that other embodiments within the spirit and scope of the invention will suggest themselves to those skilled in the art.

We claim:

1. A test device for the detection of a component in a liquid sample, the device comprising a support layer, a microporous polymer layer, one side of which facing the support, the other side of which being a side on which a sample can be applied and a reagent system for the detection of the component to be determined, the reagent system being incorporated in the polymer layer, the microporous polymer layer being a membrane which has an asymmetric pore structure with the pores narrowing toward the side to which the sample is applied, the microporous polymer layer being synthesized from a polymer selected from the group consisting of polyamides, polyether carbonates, polyacrylonitriles and polyurethanes and being produced by coagulation of a solution of the polymer, and the support layer being macroscopically smooth and impermeable to the sample.

2. A test device according to claim 1, wherein the ratio of the mean pore diameter on one surface of the membrane to that on the other membrane surface is greater than 10:1.

3. A test device according to claim 1, wherein the reagent layer is soluble or swellable in water.

4. A test device according to claim 1, wherein the ratio of mean pore diameter on one surface of the membrane to that on the other membrane surface is greater than 30:1.

5. A test device according to claim 1, wherein the support layer is a transparent polyethylene terephthalate film.

6. A test device according to claim 1, wherein the polyamides carry disulphide groups.

7. A test device according to claim 1, wherein the ratio of the mean pore diameter on the underside of the membrane to that on the membrane surface is greater than 5:1.

8. A test device according to claim 1, wherein the ratio of the mean pore diameter on the underside of the membrane to that on the membrane surface is greater than 30:1.

9. A test device according to claim 1 wherein the polymer further comprises a filler selected from the group consisting of $SiO_2$, $TiO_2$, $BaSO_4$, ZnO, cellulose and agarose powder.

10. A test device according to claim 1, wherein the component to be determined is selected from the group consisting of glucose, bilirubin, urea, proteins, ketones, triglycerides and hemoglobin.

11. A test device according to claim 1, wherein the support layer is impermeable to the sample.

12. A test device according to claim 1, wherein the polymer comprises a polymer dispersion.

13. A test device according to claim 12, wherein the polymer dispersion further comprises ionic groups.

14. A test device according to claim 12, wherein the polymer dispersion is a dispersion of an ionic polyurethane bearing an anionic group selected from the group consisting of $-SO_3^-$, $-COO^-$ and $-N^+R_3$.

15. A method for detecting a component in a liquid sample comprising bringing said sample into contact with a test device according to claim 1, said sample being applied in such a manner so that the sample enters the membrane at a surface thereof having narrower pore diameters and detecting the presence of the sample.

16. A method according to claim 15, wherein the sample is applied to the membrane surface, and the detection is observed from the membrane surface.

17. A method according to claim 15, wherein a test device having a transparent support layer is used, and the detection is observed from underneath the support layer.

* * * * *

UNITED STATES PATENT AND TRADEMARK OFFICE
CERTIFICATE OF CORRECTION

PATENT NO. : 4,824,639

DATED : April 25, 1989

INVENTOR(S) : Hildenbrand et al

It is certified that error appears in the above-identified patent and that said Letters Patent is hereby corrected as shown below:

Col. 11, line 14    Delete "3" and substitute --30--

Col. 16, line 7     Delete "anionic" and substitute --ionic--

Signed and Sealed this

Fifth Day of June, 1990

Attest:

HARRY F. MANBECK, JR.

*Attesting Officer*   *Commissioner of Patents and Trademarks*